US009492661B2

(12) United States Patent
Lerner

(10) Patent No.: US 9,492,661 B2
(45) Date of Patent: Nov. 15, 2016

(54) DEVICE AND METHODS FOR ENHANCED MULTI-DELIVERY OF BIOLOGICALLY ACTIVE SUBSTANCES INTO AN ORGANISM AND TO PREVENT LOCAL IRRITATION

(71) Applicant: Eduard N. Lerner, Amsterdam (NL)

(72) Inventor: Eduard N. Lerner, Amsterdam (NL)

( * ) Notice: Subject to any disclaimer, the term of this patent is extended or adjusted under 35 U.S.C. 154(b) by 105 days.

(21) Appl. No.: 14/245,648

(22) Filed: Apr. 4, 2014

(65) Prior Publication Data

US 2014/0221905 A1    Aug. 7, 2014

Related U.S. Application Data

(62) Division of application No. 13/321,139, filed as application No. PCT/NL2010/050287 on May 14, 2010, now Pat. No. 8,718,754.

(60) Provisional application No. 61/213,226, filed on May 19, 2009.

(51) Int. Cl.
| | |
|---|---|
| *A61N 1/30* | (2006.01) |
| *A61K 9/00* | (2006.01) |
| *A61M 31/00* | (2006.01) |
| *A61N 1/32* | (2006.01) |

(52) U.S. Cl.
CPC ............. *A61N 1/306* (2013.01); *A61K 9/0009* (2013.01); *A61K 9/0043* (2013.01); *A61M 31/00* (2013.01); *A61N 1/325* (2013.01)

(58) Field of Classification Search
CPC ................... A61K 9/0009; A61M 2210/0618; A61N 1/30; A61N 1/0432; A61N 1/0546
USPC ...... 604/20, 21, 501, 514; 607/135; 424/434
See application file for complete search history.

(56) References Cited

U.S. PATENT DOCUMENTS

| | | | | |
|---|---|---|---|---|
| 3,812,853 A | * | 5/1974 | Crain ...................... | A61M 11/00 128/200.17 |
| 5,624,898 A | * | 4/1997 | Frey, II .......................... | 514/8.4 |
| 6,001,088 A | * | 12/1999 | Roberts et al. ............... | 604/501 |
| 6,410,046 B1 | * | 6/2002 | Lerner .................. | A61K 9/0009 424/400 |
| 7,509,171 B2 | * | 3/2009 | DiMauro ........................ | 607/45 |
| 2002/0068080 A1 | * | 6/2002 | Lerner .......................... | 424/434 |
| 2002/0123678 A1 | * | 9/2002 | Lerner .................. | A61K 9/0009 600/378 |
| 2002/0183683 A1 | * | 12/2002 | Lerner .................. | A61N 1/0428 604/20 |
| 2007/0031341 A1 | * | 2/2007 | DiMauro et al. ............... | 424/45 |
| 2007/0088334 A1 | * | 4/2007 | Hillis ................... | A61B 5/0002 604/891.1 |
| 2008/0021369 A1 | * | 1/2008 | Deem .................... | A61M 29/02 604/20 |
| 2008/0167700 A1 | * | 7/2008 | Shalev et al. ................. | 607/116 |
| 2009/0209899 A1 | * | 8/2009 | Unger ............... | A61M 37/0092 604/20 |
| 2010/0030187 A1 | * | 2/2010 | Xia ............................. | 604/514 |

* cited by examiner

*Primary Examiner* — Gerald Landry, II
(74) *Attorney, Agent, or Firm* — Thomas P. O'Connell; O'Connell Law Firm

(57) ABSTRACT

Transnasal delivery of medication directly to a patient's brain is achieved using an iontophoresis wire cooperable with a medication administration device. A controller regulates an electric charge to the iontophoresis wire. The iontophoresis wire is insertable into each nasal cavity. This wire is preferably encased in a tube, through which the medication will be transnasally delivered. A cleaning solution may also be delivered to the nasal cavity after treatment to reduce irritation from the iontophoresis.

10 Claims, 2 Drawing Sheets

DEVICE AND METHODS FOR ENHANCED MULTI-DELIVERY OF BIOLOGICALLY ACTIVE SUBSTANCES INTO AN ORGANISM AND TO PREVENT LOCAL IRRITATION

RELATED APPLICATIONS

This application is a divisional application based on Application No. 13/321,139, filed Nov. 17, 2011, which was a National Stage Entry of PCT/NL2010/050287, filed May 14, 2010, which claimed priority to Provisional Application No. 61/213,226, filed May 19, 2009, each of the foregoing applications being incorporated herein by reference.

BACKGROUND OF THE INVENTION

The invention relates to non-invasive transnasal drug multi-delivery into an organism using electrotransport or phonoforesis as well as an administration device that prevents irritation of the tissue in and around the nasal cavity.

A variety of approaches currently exist for delivering biologically active agents to the central nervous system (CNS). These include, among possible others, oral administration, intravenous-, intramuscular- and transcutaneous administration. All of the above drug delivery approaches tend to be systemic, meaning that the drug is delivered into the systemic circulation, being carried to all internal organs and tissues and it has to pass through the blood-brain barrier (BBB) in order to access the CNS. Obviously, all other organs are being exposed to the drug, which may lead to a high incidence of side effects, particularly with those medications toxic to certain organs (e.g. nephrotoxic, hepatotoxic etc.). Most importantly, the therapeutic efficacy of numerous highly effective biologically active agents (e.g. large compounds, hydrophilic and charged substances such as peptides) is restricted, because they cannot or poorly penetrate the BBB, resulting in sub-therapeutic brain levels of these substances. High systemic levels have to be generated, in order to create therapeutic concentrations in the CNS, but for many therapeutic substances, even this strategy is not always effective. Therefore, there is a large interest in development of alternative drug delivery methods for the central nervous system.

In humans and primates, the olfactory epithelium or olfactory mucosa is located at the top of the nasal cavity between the central nasal septum and the lateral wall of each main nasal passage. This region of the nasal cavity, which is free of airflow, lies just under the cribriform plate of the ethmoid bone that separates the nasal and cranial cavities. In humans, the olfactory epithelium covers an area in the nose of approximately 2 $cm^2$ to 10 $cm^2$. The total olfactory surface area varies with age and between individuals. The olfactory area can be reached through the naris following the nasal septum in a superior and posterior direction. The middle turbinate, which closely opposes the septum usually prevents access to this region, fortunately, this obstruction is not surmountable.

In the last decade, a number of articles were published that describe the delivery of drugs into the brain by administering the drug in the olfactory area, and also a small number of patents have been issued that describe the use of the olfactory pathways to the brain as possible alternative drug delivery methods. For example, U.S. Pat. No. 5,624,898 issued by Frey W. H.; WO 033813A1 issued by Frey W. H.; WO 09901229A1 issued by Gizurarson S. and WO 044350A1 issued by Cevc et al. These patents all relate to the passive delivery of substances to the brain using the olfactory pathways. The agent is administered in the olfactory region, and transport of the agent is based on passive diffusion through the olfactory epithelium. However, compounds that are hydrophilic, charged and/or larger than 300 Dalton may be not delivered in therapeutic effective amounts by the methods described in the cited references. These compounds, but also all other compounds, may be delivered more rapidly and more effectively by means of a physical enhancement technique such as electrotransport as for instance has been described in U.S. Pat. Nos. 7,033,598 and 7,200,432 issued by Lerner E. N., and/or phonophoresis (sonophoresis). The use of an enhancement technique such as electrotransport has the additional advantage that it can provide a dose- and rate-controlled delivery of the biologically active agent and the dose can be pre-programmed according to individual needs.

For chronic diseases, drugs/medications may be administered everyday, sometimes times two or three times a day, for many months and years. For example, these chronic conditions include Alzheimer's disease, Parkinson's and other diseases that have to be treated for many years.

It is known that drug delivery in the skin using iontophoresis irritates the skin so another drug may be needed to treat the irritation. Using intranasal drug delivery can also irritate the tissue of the nasal cavity, and thus it has been difficult to transnasally deliver medication while preserving patient comfort.

SUMMARY OF THE INVENTION

In view of the limitation of existing CNS delivery systems, it is an object of the described embodiments to provide a method and device for enhanced and controlled administration of a biologically active agent that allows for effective concentrations of the agent in deeper tissue layers of the CNS by essentially circumventing the systemic compartment and the blood-brain barrier.

Phonoforesis may be chosen as an alternate delivery technique for the non-invasive delivery methods and devices of the present invention.

The term "iontophoresis" as used herein includes without any limitation such terms as electrotransport, iontokinesis, electroosmosis, and any combination thereof.

For transnasal medication delivery, in order to avoid irritation of the nasal cavity, after a first cycle of medication delivery is complete, another drug can be delivered to the nasal cavity that will treat the irritation of the tissue. The cyclic medication and treatment can be programmed before the process is started. In addition, further relief from irritation can be achieved with the use of an electrode such as an iontophoresis wire for delivery of the medication in combination with a passive electrode attached to the patient at an area spaced from the iontophoresis wire. After the delivery of the medication to the brain through the nasal cavity, the poles on the electrodes of the iontophoresis device will be programmed to automatically change. For example, a negative electrode on the nasal cavity (iontophoresis wire) will be changed to passive, and the passive electrode fixed on the back of the patient's head, will be changed to negative. This change, for a short duration (e.g., five to 20 minutes), will remove the irritation of the tissue in the nasal cavity. Therefore, the intranasal drug delivery route to the CNS can be used for a long time and treat chronic diseases.

In an exemplary embodiment, a device for transnasally delivering medication directly to a patient's brain includes an iontophoresis wire cooperable with a medication administration device, and a controller that regulates an electric charge to the iontophoresis wire. The iontophoresis wire is insertable into each nasal cavity through which the medication will be transnasally delivered.

The device may additionally include a delivery device for a cleaning solution. In one embodiment, the delivery device for the cleaning solution is a nose spray.

The medication administration device may include a container, such as absorbent material, holding the medication in liquid form attached to the iontophoresis wire.

In another exemplary embodiment, a method of transnasally delivering medication directly to a patient's brain includes the steps of (a) placing a medication administration tube and a cleaning solution tube in each nasal cavity through which the medication will be transnasally delivered, wherein an iontophoresis wire is cooperable with the medication administration tube; (b) securing a passive electrode to the patient, spaced from the nasal cavity; (c) delivering the medication to the nasal cavity via the medication administration tube; (d) regulating an electric charge to the iontophoresis wire; (e) after completing a cycle of steps (c) and (d), delivering a cleaning solution to the nasal cavity via the cleaning solution tube; and (f) in conjunction with step (e), reversing the electric charge on the iontophoresis wire to passive and regulating an electric charge to the passive electrode.

Step (b) may be practiced by securing the passive electrode to a back of the patient's head.

In one embodiment, step (f) is practiced after step (e). The cycle of steps (c) and (d) may be practiced to deliver a fixed amount of medication per cycle.

In yet another exemplary embodiment, a device for transnasally delivering medication directly to a patient's brain includes a medication administration tube and a cleaning solution tube for each nasal cavity through which the medication will be transnasally delivered. An iontophoresis wire is cooperable with the medication administration tube. A controller is provided with access to a source of the medication and a cleaning solution. The controller is in fluid communication with the medication administration tube and the cleaning solution tube, and the controller regulates an electric charge to the iontophoresis wire. The controller supplies the medication to the medication administration tube and the cleaning solution to the cleaning solution tube. The device also includes a passive electrode, which is securable to the patient's head spaced from the iontophoresis wire.

BRIEF DESCRIPTION OF DRAWINGS

These and other aspects and advantages of the invention will be described in detail with reference to the accompanying drawings, in which.

DETAILED DESCRIPTION OF PREFERRED EMBODIMENTS

Figure 1:
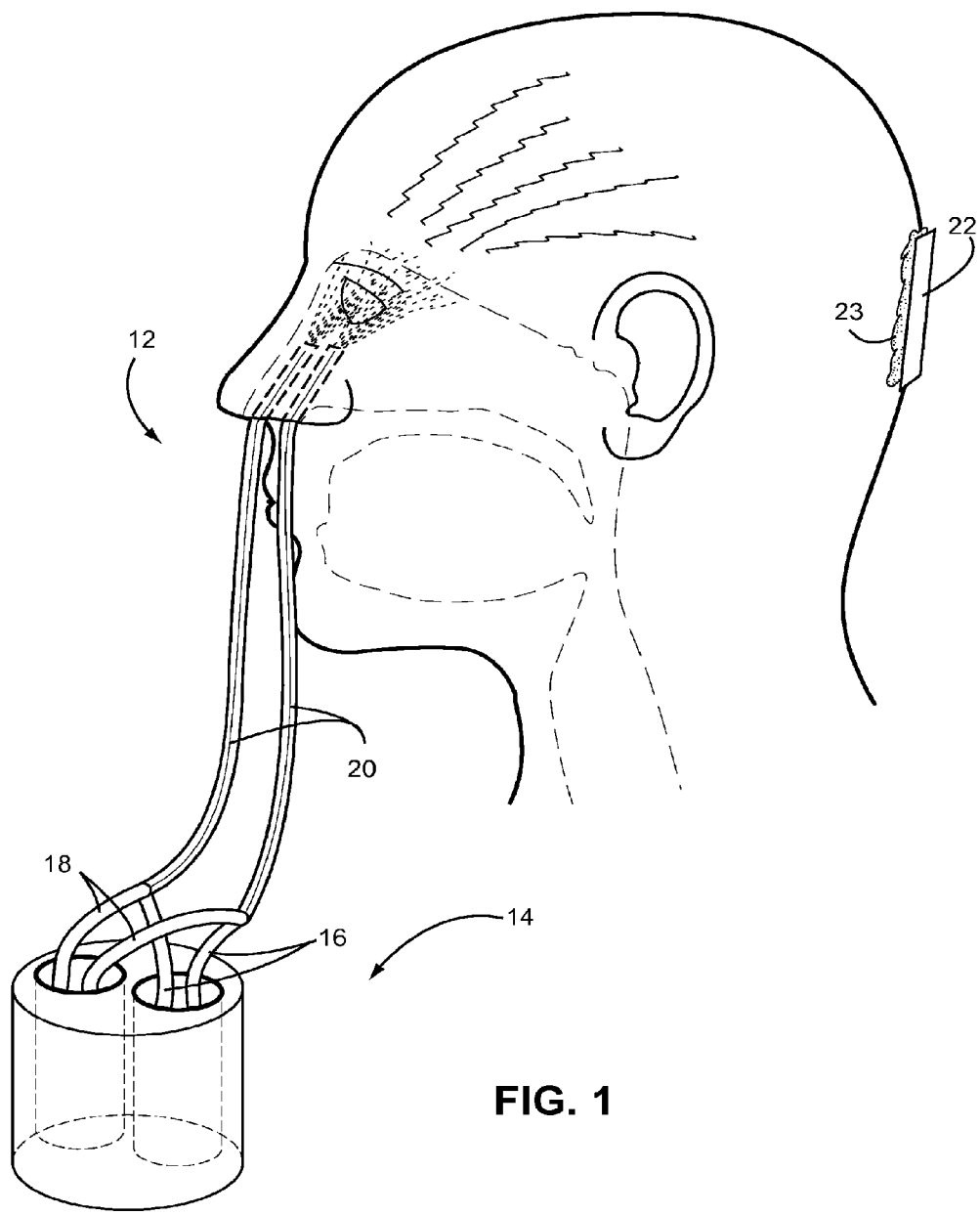
FIG. 1 shows an exemplary configuration for drug delivery.

The device according to the described embodiments is used to deliver drugs directly to the brain transnasally. The device includes an intranasal drug placement system 12 and a programmable controller/iontophoresis device 14. The intranasal medication placement system 12 works with tubes that either deliver the necessary medication or a cleaning solution or antidote. Depending on treatment there will be either two or four tubes inserted into the nasal cavity. A first tube 16 is for drug administration. A second tube 18 is for a cleaning solution (for example NaCl Sodium Chloride) or antidote to the drug for cleaning the nasal cavity in between drug administration cycles.

If the treatment requires drug administration in only one nostril (right or left), then there will be a total of two tubes. An example would be treatment of hemorrhage or thrombosis where only half of the body is paralyzed and only half of the brain would need treatment. If the brain is damaged from both sides due to (for example) Alzheimer's or Parkinson's, then both nostrils would require drug administration meaning that there are a total of four small tubes, two for each nostril (right and left).

The tubes are preferably thin, between 1 and 5 mm in diameter and are preferably composed of a soft material as to cause no irritation (for example a kind of soft plastic, or another material).

Inside the drug placement tube there is also an iontophoresis wire 20, which carries a charge. The wire 20 is preferably made of silver. It is desirable that the wire reaches exactly the end of the tube, not being shorter, but also not protruding from the tube. This is important because it must not damage the nasal tissue, but it must also be close enough to deliver the electrical charge.

The device also includes a passive electrode 22 that can be placed at the back of the patient's head. The passive electrode works in conjunction with the iontophoresis wire 20. This electrode 22 is preferably rubber coated, and a soft substance 23, such as cotton, soaked in NaCl (Sodium Chloride) to increase the effectiveness of the charge, should be interposed between the electrode 22 and the patient's head.

Figure 2:
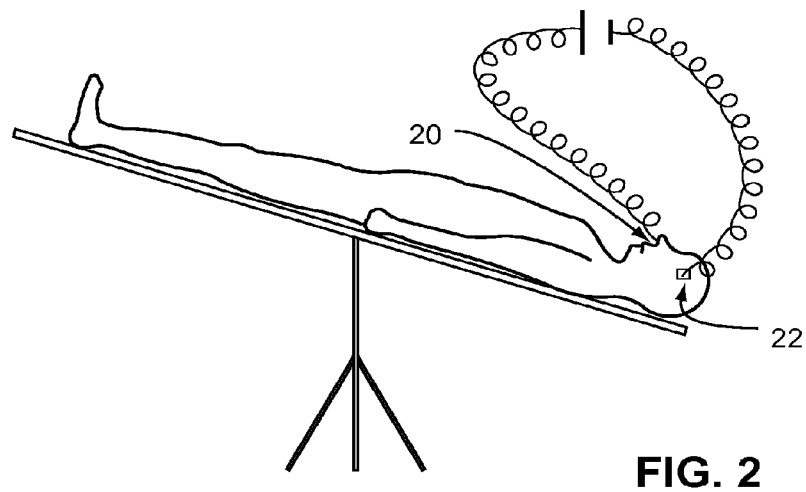
FIG. 2 shows a subject with electrodes positioned for drug delivery.
Figure 3:
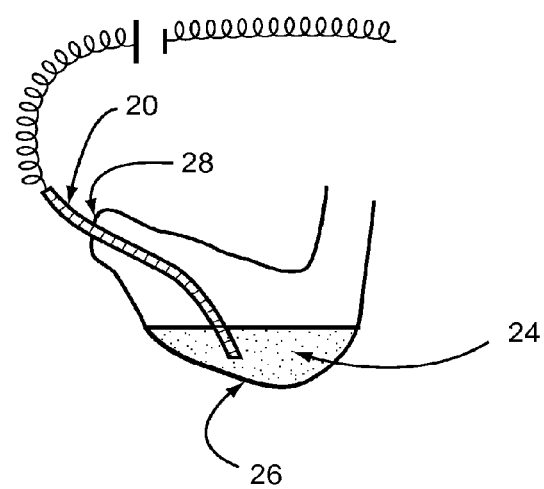
FIG. 3 is a schematic diagram of an electrode inserted into the olfactory region of the human nasal cavity.

FIG. 2 shows a patient receiving treatment, and FIG. 3 is a schematic diagram of an electrode inserted into the olfactory region of the human nasal cavity. In FIG. 3, the iontophoresis wire (active electrode) 20 is positioned in the pharmaceutical formulation 24 in the olfactory fissure adjacent the lamina cribriform (roof of the nose) 26 via the nasal entrance 28.

The intranasal drug placement system 12 will most likely need to be secured so that the tubes do not fall or slide out of the nasal cavity and so that they remain in the correct position to ensure optimal placement of the necessary medications. The tubes should therefore be fixed in a firm manner so as to ensure their correct placement. This can be done in many ways:

- The nose can be held closed by a clip so that the tubes do not slide out. This clip must be made of a material that does not cause pain when closing the nose.
- The tubes can be mounted to the patient's head with a device, which can be fixed behind the head, ears or neck. This could be done with strong elastic bands which would be fixed onto the tubes and then mounted behind the ears or neck. Another solution would be to use a brace that would wrap around the head for stability. The brace would include more than one band so that the device would not slide off the patient's head as it would be supported from all sides.
- A mask could incorporate the tubes so as to hold them in place in the nasal cavity.
- The tubes could have a small device around them which opens in the nasal cavity preventing them from sliding out.

The tubes are connected to the iontophoresis device 14, which regulates the electrical charge, pressure and dose. The medication will be transported (for example by the device applying pressure to the medication tube) to the nasal cavity, and iontophoresis will start. After a period of time, for example five minutes, the drug will again be placed in the nasal cavity, and iontophoresis will continue. After the necessary preprogrammed number of drug delivery cycles (usually between 1-10 but possibly more), the cleaning solution or antidote will be administered to help prevent irritation of the tissue (where there has been contact with the iontophoresis electrode) inside the nasal cavity. After the cleaning cycle, which would continue, for example, for about two minutes, completes two or more times, the electrical charge between the iontophoresis wire 20 and the passive electrode 22 will be inverted to further reduce the possible irritation of the nasal tissue.

The patient will go to the pharmacist to receive four parts of the device. These include the tubes 16, 18 which may be replaced on a daily basis (including the electrode wires 20 inside the medication placement tubes), the medicine and antidote, which will vary based on treatment, and finally the passive electrode 22, which will need regular replacing (for example, after every 10 or so times).

There is the possibility of not integrating the electrode wires 20 into the drug placement tubes 16. This would mean that the electrode wires 20 are fixed to the device and can be attached externally to the two tubes per nostril. Examples of how this could be accomplished are by using a clip into which the wire can be fastened. Another option would be to have a third tube into which the wire could be passed, or another possible alternative would be to tie it into place with a dedicated strap. The reason for this option would be to reduce the costs of the disposable tubes by not having to dispose of the silver wire on a daily basis. The third option for this is to clean the tube with integrated silver electrode wire daily in a basin with a disinfectant solution. In this third case, the necessity to replace the tubes would be greatly reduced, and so they would only need changing once a month or so. In any case, at least one tube will be necessary per patient at any one time.

The device will deliver a fixed amount of drug solution per drug placement cycle e.g., 1 ml. The dose will therefore be dependent on the concentration prescribed by the doctor. For example, in a flacon of 5 ml containing 1 g of the necessary drug, each drug placement cycle (1 ml) will effectively deliver 200 mg.

In an alternative embodiment, transnasal delivery can also be realized with a simpler non-automated approach. This embodiment would still require the use of a programmable iontophoresis device 14, however the automated drug placement system 12 is simplified. A prepackaged small container holds the medication in liquid form in a piece of cotton or other material/container and is attached to the active iontophoresis electrode. The electrode wire is then directly inserted into the nasal cavity, carrying the medication-containing receptacle with it. The programmable iontophoresis device then runs a program similar to the medication delivery cycle in the first embodiment. Every cycle the receptacle could be replaced with a new one, so as to refresh the medication supply manually. After this, the nasal cavity is cleaned manually using a nose spray or other device.

It is desirable for the medication-containing receptacle to be shielded off on all sides except on top to prevent the medication from leaking and to ensure the medication is transported correctly via iontophoresis. Also there can be different ways to attach the receptacle to the electrode. Examples of different methods to connect the receptacle to the electrode are click on, screw on, etc. as would be apparent to those of ordinary skill in the art. An important consideration is the small size of the receptacle as it must physically pass through the nasal cavity to be placed correctly.

For both embodiments to achieve drug delivery using iontophoresis, there are two electrodes used. The first electrode (active) 20 is inserted into the nasal cavity. The charge of the active electrode however will depend on the charge of the drugs being delivered. For example, a positively charged drug will require the electrode to be positively charged. As noted, the passive electrode 22 will be placed at the back of the head.

Figure 4:
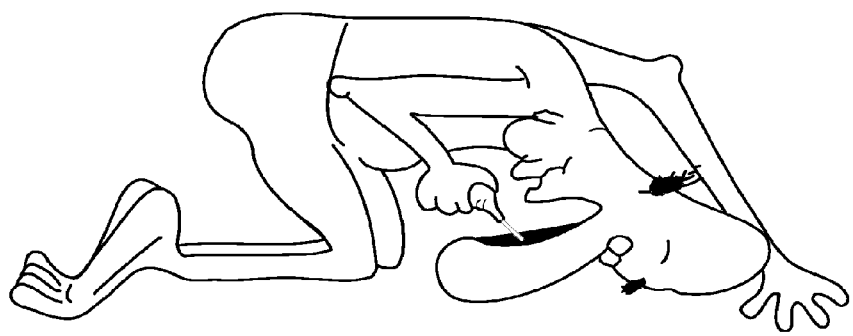
FIG. 4 shows an effective delivery position.

FIG. 4 illustrates the most effective position a patient can assume for transnasal drug delivery. This is due to the need to deliver the medication high up in the nasal cavity, reaching even the olfactory region. Humans have a small olfactory region, usually between 2-10 cm.sup.2, located at the top of the nasal cavity. To ensure that the medication does not escape through the nasopharynx to the oral region, it is therefore advisable to remain in a forwards bent over position as shown in FIG. 4. It is desirable to target the olfactory region as a drug delivery zone because it is known that the olfactory fibres transport medication through the lamina cribriform to the brain.

This method describes the delivery of drugs to the brain through the nasal cavity using an electrical charge (iontophoresis).

Into the nasal cavity, as deep as possible but without pain, the first tube 16 is inserted. The first tube 16 delivers with a spray all the drugs to the brain. A second tube 18 is similarly inserted (possibly at the same time as the first 16), and through the second tube 18, neutral solutions will be delivered, for example NaCl, which will clean the tissue in the nasal cavity after the drugs have been delivered. This is done because after the delivery of the drugs and iontophoresis, the intranasal tissue will be irritated. In the plastic tube there may also be a very small cord, which will go the end of the plastic tube in the nasal cavity. The outside portion of the cord will be connected to a battery. The electrodes 20, 22 at the front and back of the head will be connected to the battery as well as a programmed computer. The program will arrange the changing of the poles. The first tube 16 is connected to a vial of drugs under large pressure. The second tube 18 is connected to a vial of neutral drugs, which will also be under large pressure.

Another variant is that tube 16, the end which is inserted in the nasal cavity, will have piece of cotton so that when the drug is delivered it will go into the cotton. The electric charge will push the drug from the cotton into the brain.

These devices and procedures will prevent irritation in the nasal cavity using specially delivered medications to clean the tissue after iontophoresis. Also, changing the polarity will allow the use of drug delivery through the nasal cavity to the brain for many months and years.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A device for transnasally delivering medication directly to a patient's brain, the device comprising: an iontophoresis wire cooperable with a medication administration device, the iontophoresis wire being insertable into each nasal cavity through which the medication will be transnasally delivered; a controller regulating an electric charge to the iontophoresis wire, and a delivery device for a cleaning solution wherein the medication administration device comprises a container holding the medication in liquid form attached to the iontophoresis wire.

2. A device for transnasally delivering medication according to claim 1, wherein the delivery device for the cleaning solution comprises a nose spray.

3. A device for transnasally delivering medication according to claim 1, wherein the container comprises an absorbent material.

4. A device for transnasally delivering medication directly to a patient's brain, the device comprising: a medication administration tube and a cleaning solution tube for each nasal cavity through which the medication will be transnasally delivered; an iontophoresis wire cooperable with the medication administration tube; a controller with access to a source of the medication and a cleaning solution, wherein the controller is in fluid communication with the medication administration tube and the cleaning solution tube, and wherein the controller regulates an electric charge to the iontophoresis wire, the controller supplying the medication to the medication administration tube and the cleaning solution to the cleaning solution tube; and a passive electrode.

5. A device for transnasally delivering medication according to claim 4, wherein the iontophoresis wire is disposed within the medication administration tube.

6. A device for transnasally delivering medication according to claim 4, wherein the controller is programmed to regulate a pressure and a dose of the medication.

7. A device for transnasally delivering medication according to claim 4, wherein the electric charge on the iontophoresis wire is dependent on a charge of the medication being delivered.

8. A device for transnasally delivering medication according to claim 4, wherein the passive electrode is rubber coated, and wherein the device further comprises a soft substance positionable between the passive electrode and the patient's head, the soft substance being soaked in sodium chloride.

9. A device for transnasally delivering medication directly to a patient's brain, the device comprising: an iontophoresis wire cooperable with a medication administration device, the iontophoresis wire being insertable into each nasal cavity through which the medication will be transnasally delivered; a controller regulating an electric charge to the iontophoresis wire, and a delivery device for a cleaning solution wherein the device has a first set of tubes comprising a first tube that comprises the medication administration device for delivering the medication to a first nasal cavity and a second tube that comprises the delivery device for the cleaning solution for delivering the cleaning solution to the first nasal cavity and wherein the iontophoresis wire is cooperable with the first tube.

10. The device of claim 9 wherein the device further comprises a second set of tubes comprising a first tube that comprises the medication administration device for delivering the medication to a second nasal cavity and a second tube that comprises the delivery device for the cleaning solution for delivering the cleaning solution to the second nasal cavity and wherein a second iontophoresis wire is cooperable with the first tube of the second set of tubes.

* * * * *